(12) United States Patent
Sun et al.

(10) Patent No.: US 11,702,454 B2
(45) Date of Patent: Jul. 18, 2023

(54) MULTIVALENT PLANT IMMUNE FUSION PROTEIN, PRODUCTION METHOD THEREOF AND ITS USE

(71) Applicant: Suzhou Yishuimo Biological Technology Co., LTD, Jiangsu (CN)

(72) Inventors: Aiyou Sun, Jiangsu (CN); Zhong Wang, Jiangsu (CN); Zengying Cai, Jiangsu (CN); Qun Yu, Jiangsu (CN); Zhiwei Li, Jiangsu (CN); Bing Sun, Jiangsu (CN); Chong Zhang, Jiangsu (CN); Shiyue Miao, Jiangsu (CN)

(73) Assignee: Suzhou Yishuimo Biological Technology Co., LTD, Suzhou (CN)

( * ) Notice: Subject to any disclaimer, the term of this patent is extended or adjusted under 35 U.S.C. 154(b) by 0 days.

(21) Appl. No.: 17/503,356

(22) Filed: Oct. 17, 2021

(65) Prior Publication Data

US 2023/0053680 A1     Feb. 23, 2023

(30) Foreign Application Priority Data

Aug. 6, 2021   (CN) .......................... 202110901775.6

(51) Int. Cl.
  *C07K 14/27*   (2006.01)
  *A01N 37/46*   (2006.01)
  *C07K 14/37*   (2006.01)
(52) U.S. Cl.
  CPC .............. *C07K 14/27* (2013.01); *A01N 37/46* (2013.01); *C07K 14/37* (2013.01); *C07K 2319/00* (2013.01)
(58) Field of Classification Search
  CPC .... C07K 14/27; C07K 14/37; C07K 2319/00; A01N 37/46
  See application file for complete search history.

(56) References Cited

U.S. PATENT DOCUMENTS

| 5,776,889 | A | * | 7/1998 | Wei | ......................... | A61P 37/02 |
| | | | | | | 424/93.4 |
| 5,849,868 | A | * | 12/1998 | Beer | ...................... | C07K 14/27 |
| | | | | | | 530/324 |
| 2010/0233124 | A1 | | 9/2010 | Stewart et al. | | |

FOREIGN PATENT DOCUMENTS

CN          113087804 A        7/2021

OTHER PUBLICATIONS

Koonin et al., Chapter 2 Evolutionary Concept in Genetics and Genomics, Sequence—Evolution—Function: Computational Approaches in Comparative Genomics. Boston: Kluwer Academic; 2003; NCBI Bookshelf; attached as pdf, 25 pages (Year: 2003).*

(Continued)

*Primary Examiner* — Randall L Beane

(57) ABSTRACT

The present invention belongs to the field of biotechnology, in particular to a multivalent fusion protein AB-NAC-189, method for producing the same, and uses thereof. The protein AB-NAC-189 is a fusion of a polypeptide segment AB, nascent polypeptide-associated complex (NAC), and a protein 189 corresponding to amino acids 1-189 from the N-terminal of protein HarpinEa. The fusion has the properties of a multivalent plant immune protein, thus it can effectively stimulate the hypersensitive response of tobacco leaves and has good thermal stability. While stimulating the immune response of plants, it can also improve the disease resistance of plants and promote plant growth. The AB-NAC-189 multivalent vaccine shows higher activity per unit concentration, and greater ability to promote growth of wheat and tobacco; meanwhile it can significantly promote chlorophyll synthesis in Goji berry, thereby improving the yield and quality of Goji berries.

5 Claims, 7 Drawing Sheets

Figure 1:
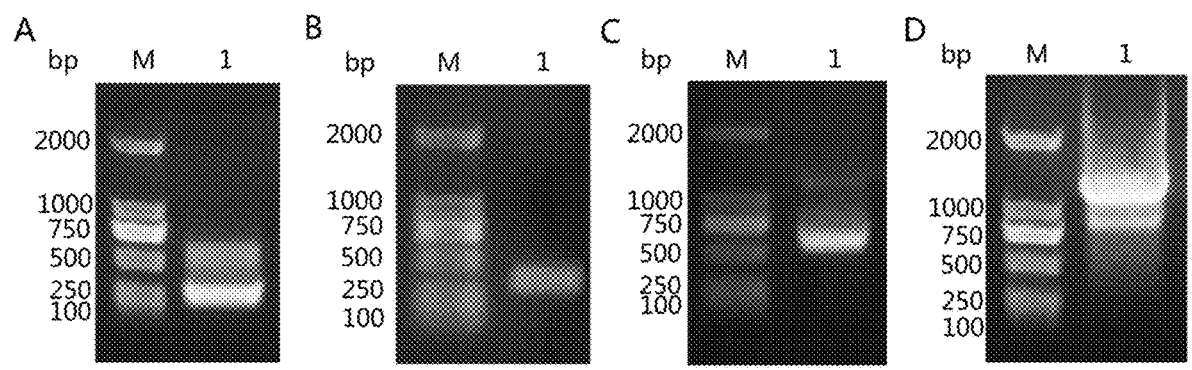

Specification includes a Sequence Listing.

(56) References Cited

OTHER PUBLICATIONS

Webber et al., Genes and homology, Current Biology, vol. 14(9):R:332-R333 (May 4, 2004) (Year: 2004).*
Rost, Twilight zone of protein sequence alignments, Protein Engineering, vol. 12(2):85-94 (1999) (Year: 1999).*

* cited by examiner

MULTIVALENT PLANT IMMUNE FUSION PROTEIN, PRODUCTION METHOD THEREOF AND ITS USE

CROSS REFERENCE TO THE RELATED APPLICATIONS

This application is based upon and claims priority to Chinese Patent Application No. 202110901775.6, filed on Aug. 6, 2021 the entire contents of which are incorporated herein by reference.

REFERENCE TO SEQUENCE LISTING

A Sequence Listing is submitted as an ASCII formatted text file via EFS-Web, with a file name of "Sequence_Listing.TXT", a creation date of Oct. 15, 2021, and a size of 8,451 bytes. The Sequence Listing filed via EFS-Web is part of the specification and is incorporated in its entirety by reference herein.

FIELD OF TECHNOLOGY

The present disclosure belongs to the field of biotechnology, and relates to a multivalent plant immune fusion protein, construction of a genetically engineered bacterium thereof, and preparation and uses of the protein. The invention relates in particular to a multivalent fusion protein AB-NAC-189, gene sequences and preparation method thereof, and its uses in improving immunity and stress resistance in plants, and promoting germination and growth thereof.

BACKGROUND

Gene $Hpal_{Xoo}$(=hrfA), cloned from the JxoIII stain of *Xanthomonas oryzae* pv. *oryzae* by PCR, encodes a 15.6-kDa protein $Harpin_{Xoo}$, the smallest Harpin protein that shares biological activities with other Harpins. The $Harpin_{Xoo}$ protein can initiate simultaneously hypersensitive cell death (HCD) and disease-resistance signaling pathways in tobacco, and hypersensitive cell death (HCD) may be induced in plants by factors such as pathogens or elicitors.

*Alternaria* sp. is known as a major plant pathogenic fungus that can cause a variety of plant diseases. The nascent polypeptide-associated complex (NAC) isolated from this fungus is composed of two subunits, α-NAC and β-NAC. Both in vivo and in vitro experiments have demonstrated that NAC (especially α-NAC) can form a stable heterologous complex which prevents nascent polypeptides from inappropriate binding to protein molecules during the process of protein translation. NAC has dual functions in protein translation and gene transcription while serving as a bridge for transporting nascent polypeptides from the cytoplasm into the endoplasmic reticulum and mitochondria. Moreover, there has been a rapid development in recent years in the research of NAC promoting plant growth and inducing immunity in plants. For example, NAC can enhance the accumulation of chlorophyll in tobacco cells, thus promoting plant growth; it can also significantly promote the formation of floral organs and seed development, enhance the survival capability of plants under stresses like salinity and drought, and promote the production of phenylalanine ammonia lyase (PAL), peroxidase (POD), polyphenol oxidase (PPO), etc. in plants for a significant induction of plant immune response among others.

The hypersensitive protein $Harpin_{Ea}$ encoded by HrpN gene, was isolated from *Erwinia amylovora* by Zhongmin Wei et al. in 1992 and can elicit the hypersensitive response in plants. The HrpN protein is one of the three members of the Harpin family. The $Harpin_{Ea}$ protein can elicit multiple resistance mechanisms early on in its induction of resistance in plants and cause a broad-spectrum resistance of plants to pathogens. Extensive research has shown that three transduction pathways are involved in the elicitation of plant defenses by $Harpin_{Ea}$, i.e., the ethylene signaling pathway, the abscisic acid signaling pathway and systemic acquired resistance.

The inventors of the present disclosure finds that the fusion and subsequent expression of the core fragments of the above-mentioned three protein molecules (AB, NAC and HrpN189) allow the fused protein to bind to multiple receptors in plant cells so as to achieve the effects of a multivalent immunoprotein with multiple functions.

SUMMARY

The present invention provides a multivalent plant immune fusion protein designated as protein AB-NAC-189, which is produced by the fusion of the following: a polypeptide segment AB encoded by a $Hpal_{Xoo}$ gene from *Xanthomonas oryzae pv. Oryzae*(Xoo), an alpha subunit of nascent polypeptide-associated complex (NAC) from *Alternaria* sp., and an amino acid sequence HrpN189 comprising amino acids 1-189 from the N-terminus of a HrpN protein from *Erwinia amylovora*.

The protein AB-NAC-189 specifically comprises one of the following:

(1) an amino acid sequence as shown in SEQ ID NO: 1; or (2) an amino acid sequence that is 75% or more homologous to the amino acid sequence of SEQ ID NO: 1; or (3) an amino acid sequence having the same function as the amino acid sequence of SEQ ID NO: 1, obtained from substitution and/or deletion and/or insertion of one or more amino acids on the basis of the amino acid sequence of SEQ ID NO: 1.

The present invention also protects nucleic acid molecules encoding the AB-NAC-189 protein, wherein the nucleic acid molecules may be DNA, such as cDNA, genome DNA, or recombinant DNA; the nucleic acid molecules may also be RNA, such as mRNA or hnRNA;

In further embodiments, the gene encoding the AB-NAC-189 protein is as shown in SEQ ID NO: 2.

The other object of the present invention is to provide an expression cassette, a recombinant vector and a recombinant bacterium, wherein the expression cassette, the recombinant vector and the recombinant bacterium comprise the gene encoding the AB-NAC-189 protein.

In further embodiments, the expression vector of the recombinant vector may be one selected from the group comprising a pET28a plasmid, a pET30a plasmid and a pBV222 plasmid.

In further embodiments, the expression vector of the recombinant vector is a pET28a(+) plasmid containing a strong promoter T7.

In further embodiments, the host of the recombinant bacterium may be one selected from the group comprising the following strains of *E. coli*: DH5α, BL21, BL21(DE3), K-12, C802, JM109, TOP10, HB101 and DH10B etc.

In further embodiments, the host of the recombinant bacteria is *E. coli* BL21(DE3).

The present invention also provides a method for constructing the above-mentioned recombinant bacterium, wherein the method comprises obtaining the recombinant bacterium by fusing the codon-optimized AB-, NAC- and HrpN189-encoding genes, separately or together, to obtain an AB-NAC-189 gene, which is then introduced into a host cell through transformation after enzymatic ligation with an expression vector.

The nucleotide sequence of the gene encoding the fragment AB is as shown in SEQ ID NO: 3.

The nucleotide sequence of the gene coding the fragment NAC is as shown in SEQ ID NO: 4.

The nucleotide sequence of the gene coding the fragment HrpN189 is as shown in SEQ ID NO: 5.

In further embodiments, the fusion of the genes encoding the fragments AB, NAC and HrpN189 is performed by joining the fragments together through the linker $(G_4S)_3$; the obtained nucleotide sequence after fusion is as shown in SEQ ID NO: 2.

In further embodiments, the recombinant bacterium is constructed by using pET28a(+) plasmid containing a strong promoter T7 as the vector, and *E. coli* BL21(DE3) as the host, to obtain a genetically engineered bacterium *E. coli*/AB-NAC-189.

The present invention also provides a method for producing the fusion protein AB-NAC-189, specifically as follows:

inoculating the successfully constructed and genetically engineered bacteria *E. coli*/AB-NAC-189 into a fermentation medium, and adding IPTG to induce expression when $OD_{600}$ reaches 0.6-1.8, harvesting the bacteria cells by centrifugation, lysing the cells and taking the supernatant for purification by Ni-NTA affinity chromatography to obtain a purified AB-NAC-189 protein product with a purity of over 90%.

In further embodiments, the culture conditions comprise: inoculating the fermentation medium with an inoculum size of 1-10%, adding IPTG as $OD_{600}$ reaches 0.6-1.8 to give a final concentration of 0.1-0.6 mM for low-temperature induction at 15-20° C. and 200 rpm for 16-20 h; after induction for 16-20 h, the yield of AB-NAC-189 protein may reach 0.1-0.8 g/L fermentation broth.

In further embodiments, the fermentation medium is LB medium with 50 μg/mL kanamycin.

In further embodiments, IPTG is added to a final concentration of 0.3 mm.

The present invention also provides a method of the AB-NAC-189 protein in promoting plant growth.

In further embodiments, method of the AB-NAC-189 in promoting plant growth comprises:

preparing a solution of the AB-NAC-189 protein with a final concentration of 0.125-50 μg/mL, alone or mixed with chemical pesticides, or other pesticides/microbial fertilizers/soil conditioners/plant stimulants/plant extracts, etc., and performing foliar sprays or root irrigation so as to effectively elicit the immune response in plants.

In further embodiments, the concentration of the AB-NAC-189 protein is 0.25 μg/mL.

In further embodiments the application method is foliar sprays.

The present invention also provides a use of the AB-NAC-189 protein in preparation of plant-growth promoters.

The present invention also provides a use of the gene encoding the AB-NAC-189 protein, or the use of the recombinant vector and the recombinant bacterium containing the encoding gene in plant growth promotion.

The present invention also provides the use of the gene encoding the AB-NAC-189 protein, or the use of the recombinant vector and the recombinant bacterium containing the encoding gene in preparation of plant-growth promoters.

In further embodiments, the plant is one selected from the group consisting of wheat, rice, tobacco, pepper, tomato, etc.

The above-mentioned uses could lead to a rapid elicitation of immune responses in plants, thus improving their disease resistance, promoting plant growth and increasing fruit yield.

BENEFICIAL EFFECTS

The multivalent fusion protein AB-NAC-189 provided in the present invention has properties of a multivalent plant immunoprotein: it can effectively elicit the hypersensitive response (HR) in tobacco leaves, and maintains immune activity after boiling in boiling water (100° C.) for 10 minutes, demonstrating a good thermal stability. Besides of eliciting immune responses in plants, it also improves the disease resistance in plants and promotes plant growth.

Compared with AB, NAC and HrpN189 individually, the AB-NAC-189 multivalent vaccine shows a higher activity per unit concentration, greater capability to promote growth of wheat and tobacco, higher capability in improving the disease resistance in tobacco by eliciting the salicylic acid (SA) pathway in tobacco, which leads to a significant promoting effect in chlorophyll synthesis in Wolfberry (Goji berry), thereby improving the yield and quality of wolfberries.

BRIEF DESCRIPTION OF THE DRAWINGS

FIG. 1 shows the PCR verification of the AB-NAC-189 gene, wherein: (A) M is the DNA marker; lane 1 is AB; (B) M is the DNA marker; lane 1 is NAC; (C) M is the DNA marker; lane 1 is 189; (D) M is the DNA marker; lane 1 is AB-NAC-189.

FIG. 2 shows results of the Ni-NTA affinity chromatography of the AB-NAC-189 protein, wherein: M is protein marker; lane 1 is the cell lysate; lane 2 is the supernatant of the cell lysate; lane 3 is the pellet of the lysate; lane 4 is the breakthrough liquid; lane 5 is 50 mM imidazole eluate; lane 6 is 300 mM imidazole eluate.

FIG. 3 shows the hypersensitive responses (HR) in tobacco leaves to AB, NAC, 189 and AB-NAC-189, wherein: (A) shows the hypersensitive response (HR) in tobacco leaves to AB; (B) shows the hypersensitive response (HR) in tobacco leaves to NAC; (C) shows the hypersensitive response (HR) in tobacco leaves to 189; (D) shows the hypersensitive response (HR) in tobacco leaves to AB-NAC-189. 1: 12.5 μg/mL; 2: 25 μg/mL; 3: 50 μg/mL; 4: 100 μg/mL; 5: water; 6: PBS; 7: EVP; 8: Proteinase K treatment for 1 h; 9: 100° C. treatment for 10 min; 10: 200 μg/mL.

FIG. 4 shows the accumulation of chlorophyll in tobacco leaves after treatment with AB, NAC, 189 and AB-NAC-189, respectively, wherein on the horizontal axis, a denotes chlorophyll a; b denotes chlorophyll b; a+b denotes total chlorophyll. Each set of bars from left to right indicates the accumulation of chlorophyll in tobacco leaves after a 7-day treatment with EVP, AB, NAC, HrpN189 and AB-NAC-189, from left to right respectively.

FIG. 5 shows the accumulation of chlorophyll in wolfberry leaves after treatment with AB, NAC, 189 and AB-NAC-189, wherein on the horizontal axis, a denotes chlorophyll a; b denotes chlorophyll b; a+b denotes total chlorophyll. Each set of bars from left to right indicates the accumulation of chlorophyll in Wolfberry leaves after a 10-day treatment with EVP, AB, NAC, HrpN189 and AB-NAC-189, respectively.

Figure 6:
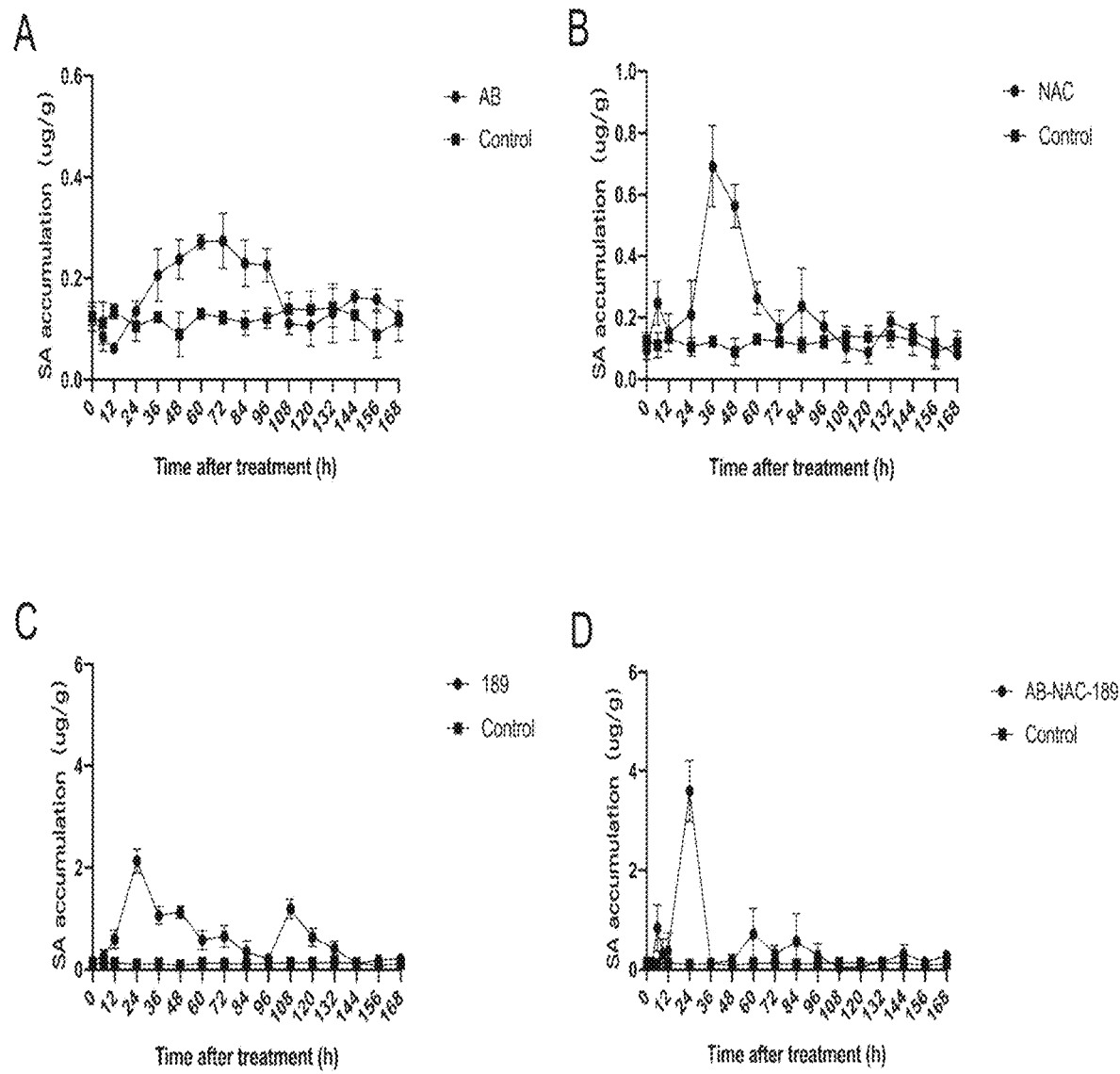

FIG. 6 shows the changes in SA accumulation in tobacco after treatment with AB, NAC, 189 and AB-NAC-189, respectively, wherein: (A) shows the changes in SA accumulation in tobacco after treatment with AB; (B) shows the changes in SA accumulation in tobacco after treatment with NAC; (C) shows the changes in SA accumulation in tobacco after treatment with 189; (D) shows the changes in SA accumulation in tobacco after treatment with AB-NAC-189.

Figure 7:
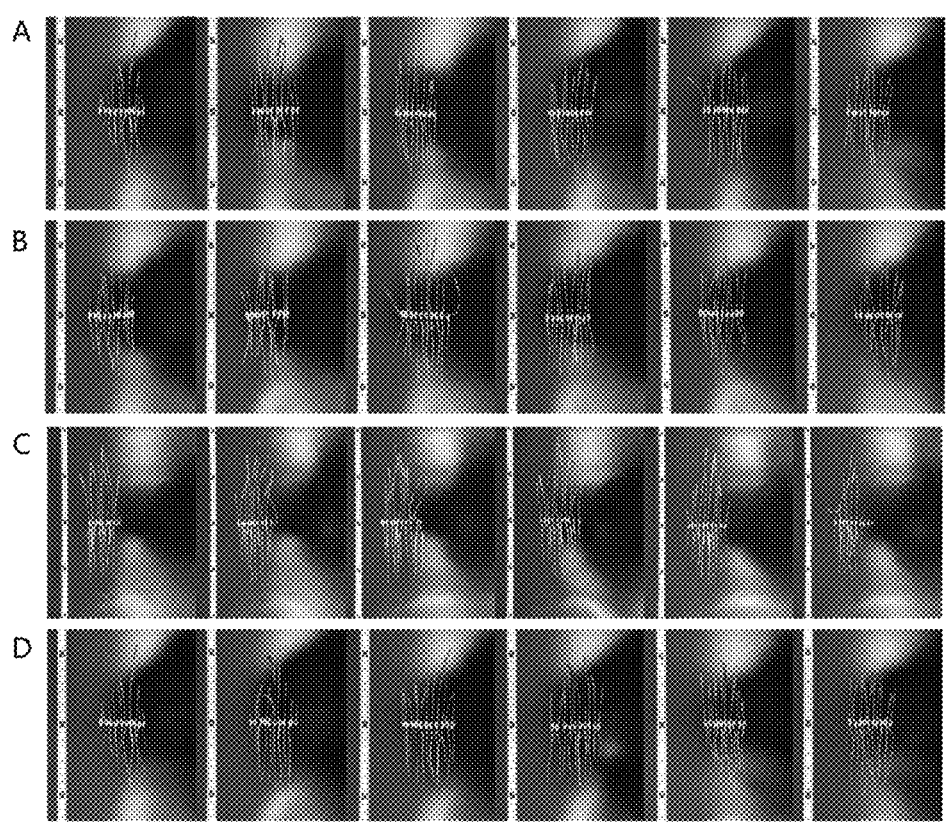

FIG. 7 shows the growth of wheat seedlings after treatment with AB, NAC, 189 and AB-NAC-189, respectively, wherein: (A) shows the growth of wheat seedlings after treatment with AB; (B) shows the growth of wheat seedlings after treatment with NAC; (C) shows the growth of wheat seedlings after treatment with 189; (D) shows the growth of wheat seedlings after treatment with AB-NAC-189. The figures from left to right denote seed soaking treatments with EVP and protein of 0.5, 2.5, 5, 25 and 50 µg/mL, respectively.

Figure 8:
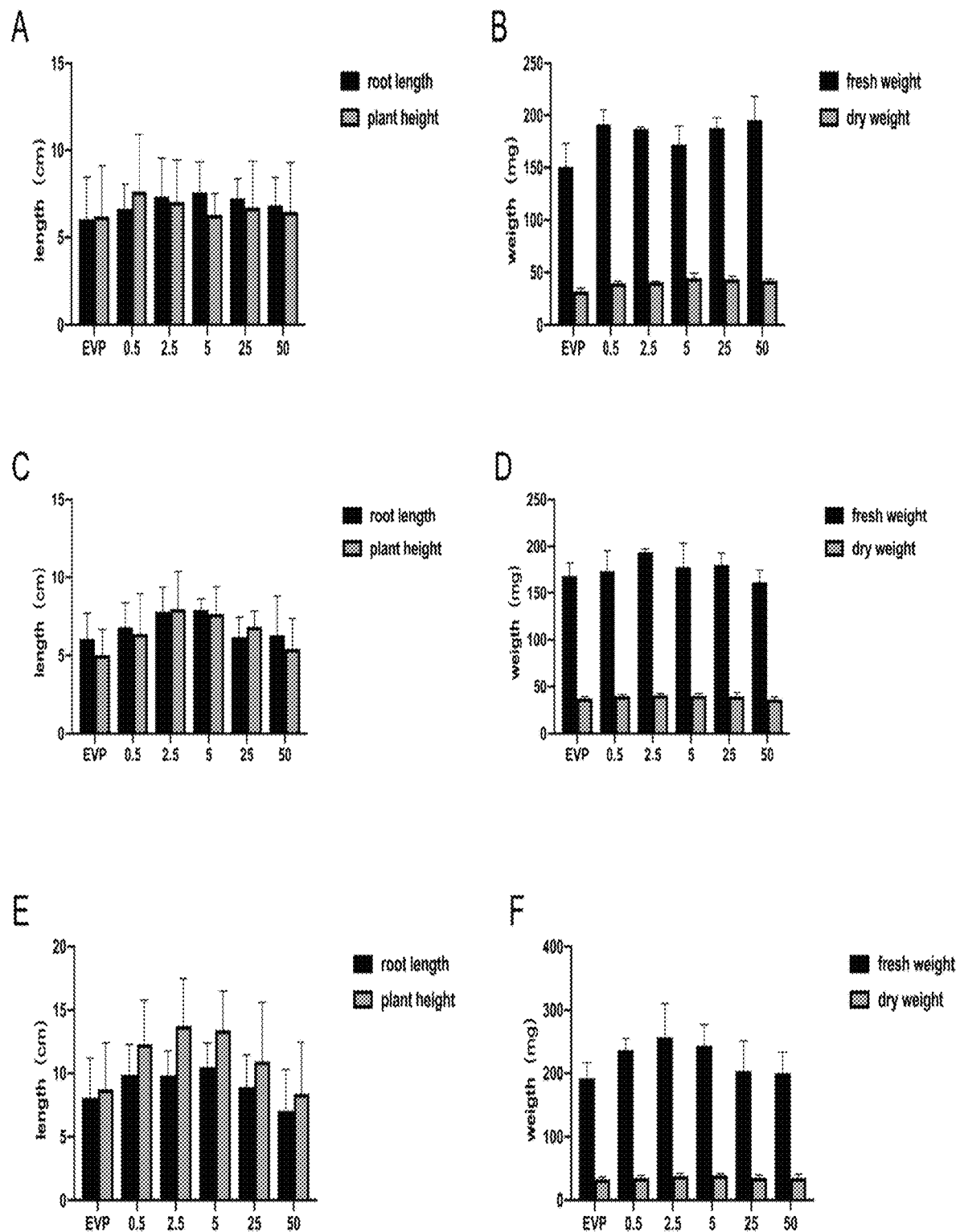
Figure 8:
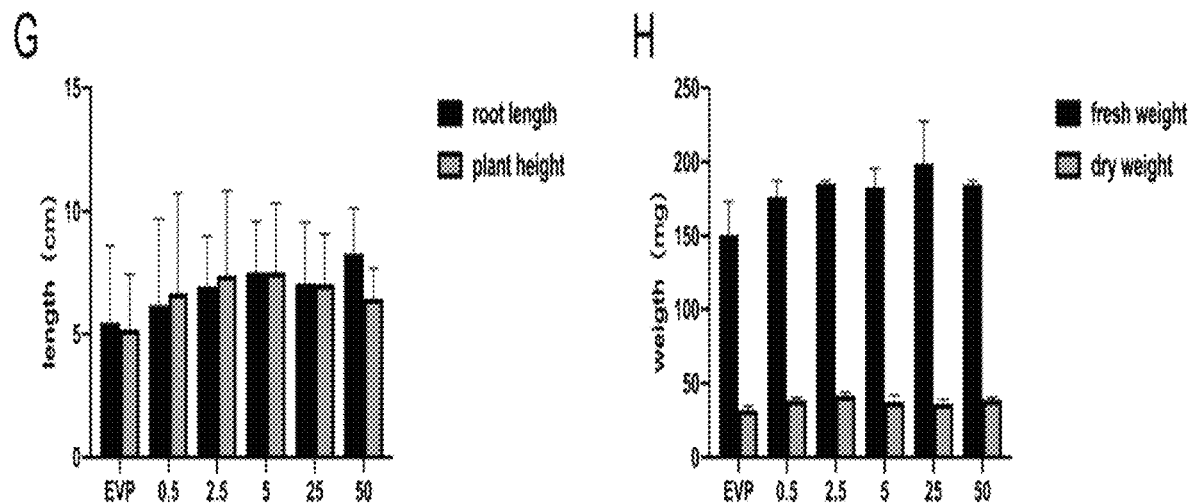

FIG. 8 shows the root length, plant height, fresh weight and dry weight of wheat seedlings after treatment with AB, NAC, 189 and AB-NAC-189, respectively, wherein: (A) shows the root length and plant height of wheat seedlings after treatment with AB; (B) shows the fresh weight and dry weight of wheat seedlings after treatment with AB; (C) shows the root length and plant height of wheat seedlings after treatment with NAC; (D) shows the fresh weight and dry weight of wheat seedlings after treatment with NAC; (E) shows the root length and plant height of wheat seedlings after treatment with 189; (F) shows the fresh weight and dry weight of wheat seedlings after treatment with 189; (G) shows the root length and plant height of wheat seedlings after treatment with AB-NAC-189; (H) shows the fresh weight and dry weight of wheat seedlings after treatment with AB-NAC-189.

Figure 9:
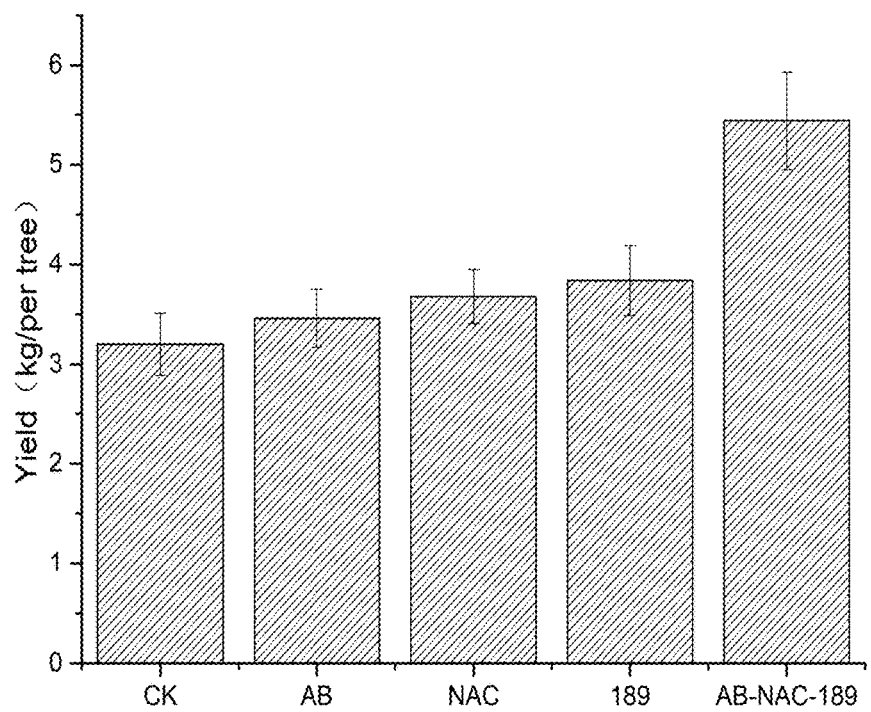

FIG. 9 shows the effect of the multivalent vaccine AB-NAC-189 in fruit yield of Goji, wherein, from left to right on the horizontal axis are samples treated with EVP, AB, NAC, HrpN189 and AB-NAC-189, respectively; the vertical axis designates the average fruit yield of Wolfberry per tree based on samples for each treatment.

DESCRIPTION OF THE EMBODIMENTS

In order to more apparently understand the objectives, technical means, and advantages of the present invention, the present invention is described hereafter through specific embodiments. It should be understood that, the description of the embodiments herein is merely for the purpose of explanation of the present invention, and does not limit the scope of the present invention.

Unless otherwise specified, the experimental methods of the following embodiments are conventional methods; and unless otherwise specified, the experimental materials and reagents used in the following embodiments are commercially available.

The AB-NAC-189 protein provided by the present invention can be either synthesized artificially based on the amino acid sequence, or obtained through biological expression of the encoding gene.

The present invention will be further explained and described with reference to the accompanying figures and embodiments hereinafter.

Embodiment 1: Construction of the Genetically Engineered Bacterium E. coli/AB-NAC-189

The AB-NAC-189 protein provided by the present invention can be either synthesized artificially based on the amino acid sequence, or obtained through biological expression of the encoding gene. The later, i.e., method using gene expression will be explained and illustrated in this exemplary embodiment.

(1) Gene Fusion

⓪ Primer Sequences

The primers used for the fusion of gene AB (as shown in SEQ ID NO: 3), gene NAC (as shown in SEQ ID NO: 4) and gene 189 (as shown in SEQ ID NO: 5) are AB FP, AB RP, NAC FP, NAC RP, and 189 FP and 189 RP, the sequences of which are as shown in the following table:

| Name | Gene Sequence | Remarks | SEQ ID NO: |
|---|---|---|---|
| AB FP | CTTTAAGAAGGAGATATA*CCATGG*GCAACTCTCT GAACACCCAGTTCGGT G | Restriction site Nco I | 6 |
| AB RP | TTTCCGGTTCGTCCGGCAGTTCTTCGATACGCGG GTTAGC*CGATCCGCCACCGCCAGAGC* | The italicized and underlined part is 20 bp (base pairs) of the linker $(G_4S)_3$. | 7 |
| NAC FP | *GCTCTGGCGGTGGCGGATCG*GCTAACCCGCGTAT CGAAGAACTGCCGGACGAACCGGAAA | The italicized and underlined part is 20 bp (base pairs) of the linker $(G_4S)_3$. | 8 |
| NAC RP | AGACCAGAGGTGTTCAGAGA*CGATCCGCCACCG CCAGAGCCACCTCCGCCTGAACCGCCTCCACC*GT CTTCGATTTTAGCTTCACCGAAGATTAT | The italicized and underlined part is 45 bp (base pairs) of the linker $(G_4S)_3$. | 9 |

| Name | Gene Sequence | Remarks | SEQ ID NO: |
|---|---|---|---|
| 189 FP | *<u>GCTCTGGCGGTGGCGGATCG</u>*TCTCTGAACACCTC TGGTCTGGGTGCTTCT | The italicized and underlined part is 20 bp (base pairs) of the linker $(G_4S)_3$. | 10 |
| 189 RP | GTGGTGGTGGTGGTGGTG*<u>CTCGAG</u>*TTTACCACC AGAAGAAGAACCCTGA | Restriction site Xho 1 | 11 |

② Gene Fusion

The AB gene was amplified with primers AB FP and AB RP, using a sequence containing the AB gene as template; gene NAC was amplified with primers NAC FP and NAC RP, using a sequence containing the NAC gene as template; and gene 189 was amplified with primers 189 FP and 189 RP, using a sequence containing the 189 gene as template. Gene fusion was performed with the amplification products (The reaction was 50 μL comprising 18 μL of water, 3 μL of the target gene, 2 μL of the forward primer, 2 μL of the reverse primer and 25 μL of 2×PFU; an initial denaturation step was performed at 94° C. for 90 seconds followed by a separate denaturation step at 94° C. for 20 seconds, an annealing step at 60° C. for 20 seconds, and an extension step at 72° C. for 41 seconds; the three steps of denaturation, annealing and extension were cycled 10 times, and a final extension step was performed for 5 min.). The AB-NAC-189 gene was created using fusion PCR with primers AB FP and 189 RP. The results of PCR amplification is shown in FIG. 1.

(2) Construction of an Engineered Bacterium

The AB-NAC-189 gene was inserted between the restriction sites Nco I and Xho I of the pET28a(+) plasmid that contains a strong promoter T7, to construct a recombinant plasmid pET-28a-AB-NAC-189. This recombinant plasmid was transformed into *E. coli* BL21(DE3) as the host bacterium, and the positive clone was identified by PCR verification and gene sequencing as the successfully-constructed and genetically engineered bacterium *E. coli*/AB-NAC-189.

Embodiment 2: Induced Expression of the Multivalent Fusion Protein AB-NAC-189

The recombinant bacterial strain *E. coli*/AB-NAC-189 was inoculated into LB medium with 50 μg/mL kanamycin and cultured overnight at 37° C. and 200 rpm for 12 hours to obtain a seed solution;

the seed solution was then inoculated into LB medium with 50 μg/mL kanamycin with an inoculum size of 5%, and kept being cultured at 37° C.; when $OD_{600}$ reached 1.0, IPTG was added to give a final concentration of 0.3 mM for low-temperature induction at 18° C. and 200 rpm for 18 h; the yield of the AB-NAC-189 protein could reach 0.8 g/L fermentation broth.

Figure 2:
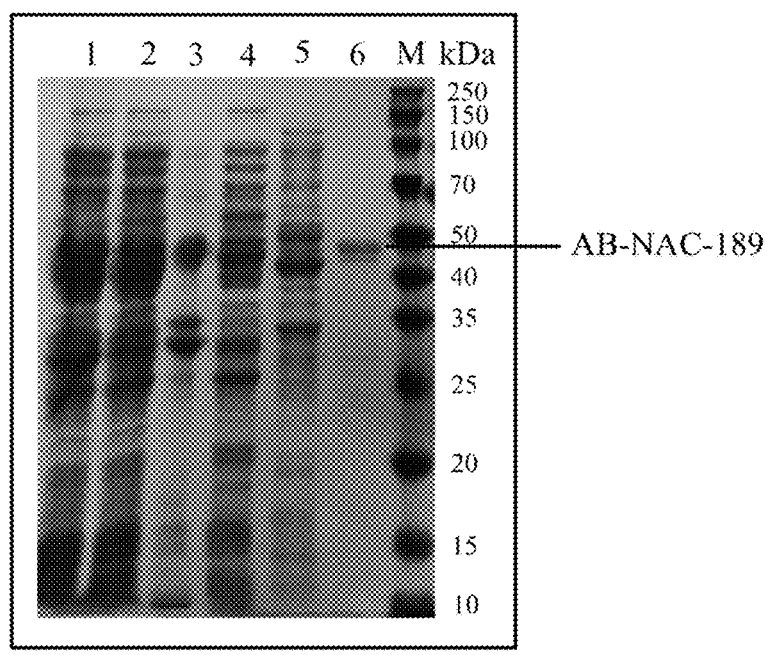

After inducing, bacterial cells were collected by centrifugation at 8000 rpm for 10 minutes, lysed, and centrifuged at 8000 rpm for 30 minutes; the supernatant was then filtered with a filtration membrane and fed into a Ni-NTA affinity chromatography column; once the protein sample in the tube was reduced by the volume of one column, the breakthrough material was taken; then the nickel column was washed with 4 column volumes of lysis buffer and eluted with 50 mM or 300 mM imidazole; and the eluate was collected. The results showed that the AB-NAC-189 protein could be eluted completely by 300 mM imidazole, giving a protein purity of around 90%. SDS-PAGE analysis was performed for the protein samples, and the results are shown in FIG. 2. It can be found that, the fusion protein AB-NAC-189 is shown clearly in lane 6 with a band size of about 48 kDa.

Embodiment 3: Assay of the Hypersensitive Response (HR) in Tobacco Leaves to AB-NAC-189

The AB, NAC, 189 and AB-NAC-189 protein products were diluted with PBS buffer respectively, and the following samples were prepared:

(A-D) sample 1: 12.5 μg/mL AB, NAC, 189 and AB-NAC-189, respectively;
(A-D) sample 2: 25 μg/mL AB, NAC, 189 and AB-NAC-189, respectively;
(A-D) sample 3: 50 μg/mL AB, NAC, 189 and AB-NAC-189, respectively;
(A-D) sample 4: 100 μg/mL AB, NAC, 189 and AB-NAC-189, respectively;
(A-D) sample 9: 200 μg/mL AB, 200 μg/mL NAC protein, 100 μg/mL 189, and 100 μg/mL AB-NAC-189 protein, respectively, each heated in a water bath of 100° C. for 10 minutes;
(A, B) sample 10: 200 μm/mL AB and NAC, respectively;
Negative Control 1 (sample 5): water;
Negative Control 2 (sample 6): PBS buffer;
Negative Control 3 (sample 7): lysis of *E. coli* with empty vector preparation (EVP);
Negative Control 4 (sample 8): protein treated with Proteinase K for 1 h.

The above-mentioned protein samples and control samples were injected into tobacco leaves in growing stage with an injection dose of 50 μL in each hole. The injected tobacco was placed in a plant incubator and incubated at 28° C. for 3 days to observe the size of the leaf spots in the leaves.

Figure 3:
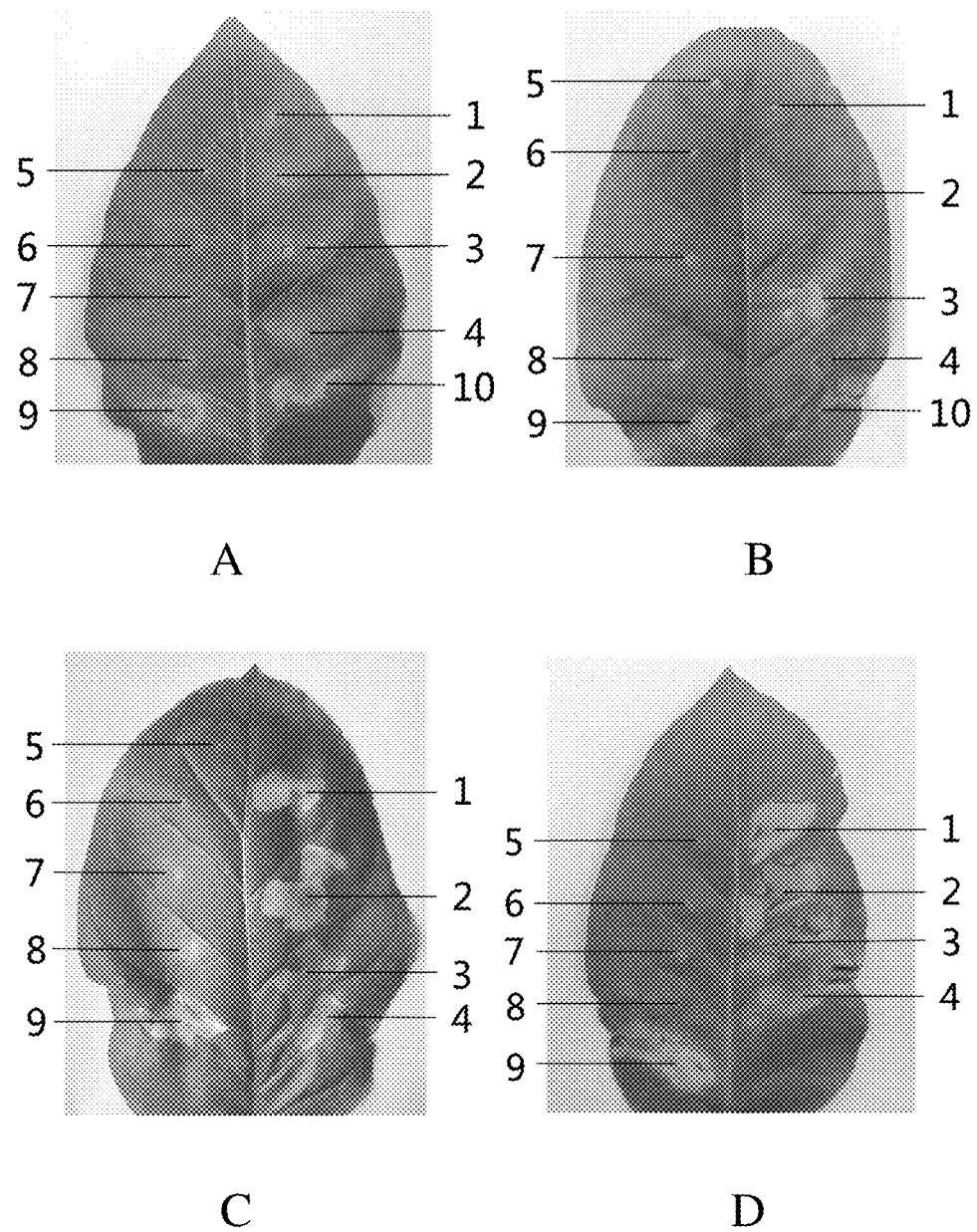

As shown by the results of figure (D) in FIG. 3, AB-NAC-189 induced a strong hypersensitive response (HR) in tobacco leaves as obvious leaf spots appeared on the tobacco leaves after the injection of 12.5 μg/mL (0.32 μM) of the AB-NAC-189 protein; the biological activities of the AB-NAC-189 protein treated in a water bath of 100° C. for 10 minutes was not affected significantly as the treated protein still caused hypersensitive response (HR) in tobacco leaves, indicating an unaffected and stable spatial structure of the multivalent immunoprotein and its potential to be produced in large quantities and put into use. It is also demonstrated in FIG. 3 that, compared to their corresponding controls with the same mass concentration (AB: 2.02 μM, NAC: 0.94 μM, 189: 0.65 μM), AB and NAC did not cause significant leaf plots, while 189 and AB-NAC-189 did, with a larger area of leaf plots caused by AB-NAC-189. Considering that the molar concentration of AB-NAC-189 was the smallest, only half that of 189, it is indicated that the fusion protein AB-NAC-189 has an activity with a better cumulative effect, thus significantly stimulating the HR response in tobacco.

Embodiment 4: Experiment on AB-NAC-189 Promoting Chlorophyll Synthesis in Tobacco 10 mL of 15 μg/mL AB, NAC, 189 and AB-NAC-189 protein products and negative control EVP were sprayed on three tobacco leaves at lower vertical position each, and samples were taken after 7 days to determine the accumulation of chlorophyll in tobacco. The contents of chlorophyll a and chlorophyll b of each sample were determined at $A_{665}$ and $A_{649}$, respectively, after adding 10 mL of 95% ethanol to 0.1 g of each sample and leaving them to stand still for 24 h protected from light.

Figure 4:
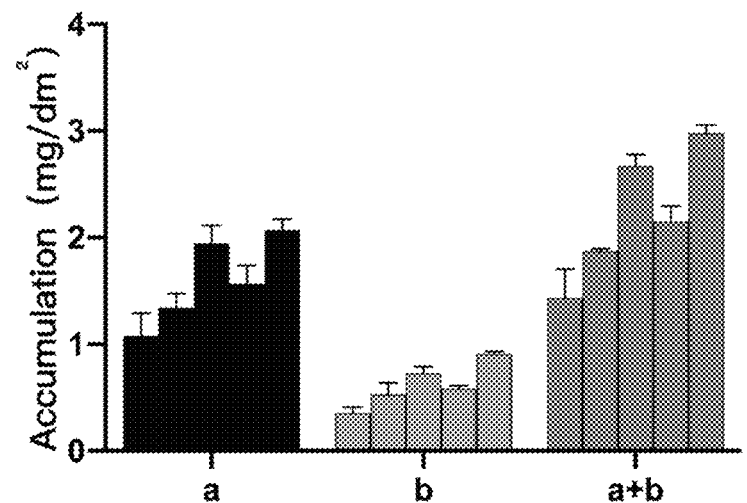

As shown by the results in FIG. 4, the accumulation of chlorophyll in tobacco after treatment with AB (2.42 μM), NAC (1.13 μM), 189 (0.78 μM) and AB-NAC-189 (0.39 μM) was approximately 1.3, 1.8, 1.5 and 1.9 times, respectively, as high as that of the corresponding negative control with the same mass concentration. As can be seen, AB-NAC-189, with the lowest molar concentration, only half that of 189, exhibited a more significant effect on promoting chlorophyll synthesis in tobacco, indicating that AB-NAC-189 has a significant and positive effect on the growth of tobacco.

Embodiment 5: Experiment on AB-NAC-189 Promoting Chlorophyll Synthesis in Goji 3 mL of 10 μg/mL AB (1.61 μM), NAC (0.75 μM), 189 (0.52 μM) and AB-NAC-189 (0.26 μM) protein products and negative control EVP, were sprayed on five Wolfberry leaves of similar size each, with 3 parallel experiments in each group, and samples were taken after 10 days to determine the accumulation of chlorophyll in Goji. The contents of chlorophyll a and chlorophyll b of each sample were determined at $A_{665}$ and $A_{649}$, respectively, after adding 10 mL of 95% ethanol to 0.1 g of each sample and leaving them to stand still for 24 h, protected from light.

Figure 5:
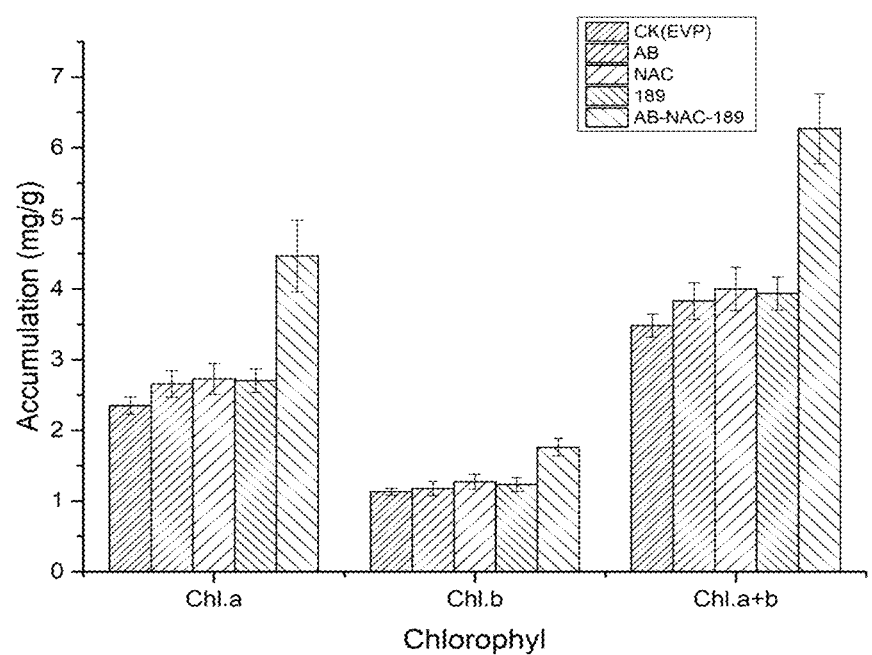

As shown by the results in FIG. 5 and Table 1, the accumulation of chlorophyll in Wolfberry after treatment with AB, NAC, 189 and AB-NAC-189 was approximately 1.1, 1.15, 1.13 and 1.8 times as high as that of the negative controls, respectively. As can be seen, AB, NAC or 189 alone did not enhance the accumulation of chlorophyll in Goji berry significantly, while AB-NAC-189, with the lowest molar concentration, significantly promoted the synthesis of chlorophyll in Goji, thus improving the yield and quality of Goji berries, which makes it a good candidate plant vaccine for the growth and production of wolfberry, with a much better effect than protein AB, NAC or189.

TABLE 1

Effects of AB-NAC-189 on chlorophyll synthesis in wolfberry leaves

| Sample | Chlorophyll a (mg/g FW) | Chlorophyll b (mg/g FW) | Total chlorophyll (mg/g FW) | Ratio (×CK$^{-1}$) (%) |
|---|---|---|---|---|
| EVP (CK) | 2.351 ± 0.122 | 1.132 ± 0.049 | 3.483 ± 0.163 | — |
| AB | 2.657 ± 0.161 | 1.174 ± 0.101 | 3.831 ± 0.219 | 110 |
| NAC | 2.727 ± 0.173 | 1.274 ± 0.105 | 4.001 ± 0.238 | 115 |
| 189 | 2.703 ± 0.167 | 1.233 ± 0.097 | 3.936 ± 0.234 | 113 |
| AB-NAC-189 | 4.467 ± 0.207 | 1.762 ± 0.123 | 6.269 ± 0.295 | 180 |

Embodiment 6: Changes of SA Accumulation after Treatment with AB-NAC-189

Tobacco plants of comparable growth were selected and sprayed uniformly with AB, NAC, 189 and AB-NAC-189 protein products of 15 μg/mL on three tobacco leaves at lower vertical position, respectively, with EVP as a negative control. Samples were taken at different times after the treatment to determine the SA accumulation in tobacco leaves by UPLC-MS method.

The results are shown in FIG. 6, demonstrating a rapid increase in SA accumulation in tobacco leaves after treatment with AB-NAC-189 (0.39 μM) with a peak of 3.59 μg/g, about 29.82 times the base level, reached in 24 h, followed by a rapid drop to the base level, and a second and third increase-followed-by-decrease occurring at about 60 h and 84 h, which indicates that AB-NAC-189 treatment elicited the SA pathway in tobacco. Meanwhile, compared with AB (2.42 μM), NAC (1.13 μM) and 189 (0.78 μM), which enhanced SA accumulation by approximately 2.25, 5.75 and 17.69 times, respectively, AB-NAC-189 demonstrated a stronger effect in eliciting the SA pathway, with SA accumulation being much bigger than the sum of that by treatment with AB, NAC and 189. According to analysis based on molar concentrations, i.e., SA accumulation elicited by each single molecule in tobacco leaves, AB-NAC-189 performed the best, with a value that was 3.37 times that of 189 which was the best among the remaining three, and 82 times that of AB which performed the worst, thus it is even more accurately demonstrated that AB-NAC-189 has a stronger capability of improving disease resistance in plants.

Embodiment 7: Experiment on AB-NAC-189 Treatment Promoting Growth of Wheat Seedlings Wheat seeds were treated by soaking in AB, NAC, protein 189, protein AB-NAC-189 of different concentrations for 12 h each, and then sown in 96-well culture boxes to grow in hydroponic culture mode for 7 d before parameter were measured. The same treatment was performed using EVP as a negative control.

The results are shown in FIGS. 7 and 8. It can be seen that compared with wheat treated with EVP, wheat treated with AB-NAC-189 exhibited root length up to 1.38 times, plant height up to 1.45 times, fresh weight up to 1.32 times, and dry weight up to 1.31 times. Moreover, compared with treatments with AB, NAC and 189, the promotion effect by AB-NAC-189 increased by about 10%, 5% and 6%, respectively, indicating a stronger growth-promoting effect on wheat by the fusion protein AB-NAC-189 than the monomeric proteins.

Embodiment 8: Experiment on AB-NAC-189 Promoting Fruit Yield of Wolfberry 25 wolfberry trees of 6 years old with comparable growth, grown from the same sown seedlings, were selected for the experiment and divided into 5 groups with 5 trees in each group. Protein products AB, NAC, 189, and AB-NAC-189 and negative control EVP solution of 300 mL each (15 μg/mL) were sprayed twice in total, once between April and May (peak period of bud emergence and new branching) and once in June (period of continued growth of new branches, bud emergence, fruit set and young fruit expansion); the yield of Goji berries was determined during the harvesting season.

As shown by the results in FIG. 9 and Table 2, the fruit yield of wolfberry treated with AB (2.42 μM), NAC (1.13 μM), 189 (0.78 μM) and AB-NAC-189 (0.39 μM) was 1.08, 1.15, 1.20 and 1.7 times as high as that of the negative control of the same mass concentration. As can be seen, there was no significant increase in fruit yield of wolfberry by treatment with AB, NAC or 189 alone. However, AB-NAC-189, with the lowest molar concentration, significantly promoted the yield of Goji berries with 70% increase in fresh weight of the fruit which was big and full, thus indicating that AB-NAC-189 is a promising candidate as a multivalent plant vaccine to improve yield and quality of Goji berries.

TABLE 2

Effects of AB-NAC-189 on Goji berries

| Sample | Yield (kg/tree) | Ratio ($\times CK^{-1}$) (%) |
|---|---|---|
| EVP (CK) | 3.2 ± 0.31 | — |
| AB | 3.46 ± 0.29 | 108 |
| NAC | 3.68 ± 0.27 | 115 |
| 189 | 3.84 ± 0.35 | 120 |
| AB-NAC-189 | 5.44 ± 0.49 | 170 |

The above embodiments are merely exemplary embodiments of the present invention described in details, and should not be considered as limiting the patent scope. It should be noted that, the above-mentioned embodiments may be carried out with a few deformation, combination and improvement by those skilled in the art in the present field within the conception of the present invention, all of which are within the protection scope of the present invention. Therefore, the protection scope of the present invention shall be subject to the claims.

SEQUENCE LISTING

<160> NUMBER OF SEQ ID NOS: 11

<210> SEQ ID NO 1
<211> LENGTH: 392
<212> TYPE: PRT
<213> ORGANISM: Artificial Sequence
<220> FEATURE:
<223> OTHER INFORMATION: The sequence is synthesized.

<400> SEQUENCE: 1

Met Gly Asn Ser Leu Asn Thr Gln Phe Gly Gly Ser Thr Ser Asn Leu
1               5                   10                  15

Gln Val Gly Pro Ser Gln Asp Thr Thr Phe Gly Ser Asn Gln Gly Gly
            20                  25                  30

Asn Gln Gly Ile Ser Glu Lys Gln Leu Asp Gln Leu Leu Cys Gln Leu
        35                  40                  45

Ile Ser Ala Leu Leu Gln Ser Ser Lys Asn Ala Glu Gly Gly Gly Gly
    50                  55                  60

Ser Gly Gly Gly Gly Ser Gly Gly Gly Ser Ala Asn Pro Arg Ile
65                  70                  75                  80

Glu Glu Leu Pro Asp Glu Pro Glu Lys Lys Asn Val Gln Ile Glu Glu
                85                  90                  95

Asp Glu Ser Ser Asp Glu Ser Glu Gly Glu Glu Gly Glu Val Ser Val
            100                 105                 110

Pro Ala Gly Ser Ser Val Ala Val His Ser Arg Asn Glu Lys Lys Ala
        115                 120                 125

Arg Lys Ala Ile Ala Lys Leu Gly Leu Lys His Ile Asp Gly Ile Thr
    130                 135                 140

Arg Val Thr Leu Arg Arg Pro Lys Asn Ile Leu Phe Val Ile Asn Gln
145                 150                 155                 160

Pro Asp Val Tyr Lys Ser Pro Ser Ser Asn Thr Trp Ile Ile Phe Gly
                165                 170                 175

Glu Ala Lys Ile Glu Asp Gly Gly Gly Ser Gly Gly Gly Gly Ser
            180                 185                 190

Gly Gly Gly Gly Ser Ser Leu Asn Thr Ser Gly Leu Gly Ala Ser Thr
        195                 200                 205

```
Met Gln Ile Ser Ile Gly Gly Ala Gly Gly Asn Asn Gly Leu Leu Gly
    210             215                 220
Thr Ser Arg Gln Asn Ala Gly Leu Gly Gly Asn Ser Ala Leu Gly Leu
225             230                 235                 240
Gly Gly Gly Asn Gln Asn Asp Thr Val Asn Gln Leu Ala Gly Leu Leu
                245                 250                 255
Thr Gly Met Met Met Met Ser Met Met Gly Gly Gly Gly Leu Met
            260                 265                 270
Gly Gly Gly Leu Gly Gly Gly Leu Gly Asn Gly Leu Gly Gly Ser Gly
                275                 280                 285
Gly Leu Gly Glu Gly Leu Ser Asn Ala Leu Asn Asp Met Leu Gly Gly
    290                 295                 300
Ser Leu Asn Thr Leu Gly Ser Lys Gly Gly Asn Asn Thr Thr Ser Thr
305             310                 315                 320
Thr Asn Ser Pro Leu Asp Gln Ala Leu Gly Ile Asn Ser Thr Ser Gln
                325                 330                 335
Asn Asp Asp Ser Thr Ser Gly Thr Asp Ser Thr Ser Asp Ser Ser Asp
                340                 345                 350
Pro Met Gln Gln Leu Leu Lys Met Phe Ser Glu Ile Met Gln Ser Leu
            355                 360                 365
Phe Gly Asp Gly Gln Asp Gly Thr Gln Gly Ser Ser Ser Gly Gly Lys
    370                 375                 380
Leu Glu His His His His His His
385                 390

<210> SEQ ID NO 2
<211> LENGTH: 1179
<212> TYPE: DNA
<213> ORGANISM: Artificial Sequence
<220> FEATURE:
<223> OTHER INFORMATION: The sequence is synthesized.

<400> SEQUENCE: 2
atgggcaact ctctgaacac ccagttcggt ggttctacct ctaacctgca ggttggtccg    60
tctcaggaca ccaccttcgg ttctaaccag ggtggtaacc agggtatctc tgaaaaacag   120
ctggaccagc tgctgtgcca gctgataagt gctctgctgc agtcttctaa aaacgctgaa   180
ggtggaggcg ttcaggcgg aggtggctct ggcggtggcg gatcggctaa cccgcgtatc   240
gaagaactgc cggacgaacc ggaaaaaaaa aacgttcaga tagaagaaga cgaatcttct   300
gacgaatctg aaggtgaaga aggtgaagtt tctgttccgg ctggttcttc tgttgctgtt   360
cactctcgta acgaaaaaaa agctcgtaaa gctatcgcta aactgggtct gaaacacatc   420
gacggtatca cccgtgttac cctgcgtcgt ccgaaaaaca tcctgttcgt tatcaaccag   480
ccagacgtgt acaaaagccc gtcttctaac acctggataa tcttcggtga agctaaaatc   540
gaagacggtg aggcggttc aggcggaggt ggctctggcg gtgcggatc gtctctgaac   600
acctctggtc tgggtgcttc taccatgcag ataagtatcg gtggtgctgg tggtaacaac   660
ggtctgctgg gtacttctcg tcagaacgct ggtctgggtg gtaactctgc tctgggtctg   720
ggtggtggta accagaacga caccgttaac cagctggctg gtctgctgac cggtatgatg   780
atgatgatgt ctatgatggg tggtggtggt ctgatgggtg gtggtctggg tggtggtctg   840
ggtaacggtc tgggtggttc tggtggtctg ggtgaaggtc tgtctaacgc tctgaacgac   900
atgctgggtg gttctctgaa cacccctgggt tctaaaggtg gtaacaacac cacctctacc   960
accaactctc cgctggacca ggctctgggt atcaactcta cctctcagaa cgacgactct   1020
```

```
acctctggta ctgactctac ctctgactct tctgacccga tgcagcagct gctgaaaatg    1080
ttctctgaaa tcatgcagtc tctgttcggt gacggtcagg acggtactca gggttcttct    1140
tctggtggta aactcgagca ccaccaccac caccactga                           1179
```

<210> SEQ ID NO 3
<211> LENGTH: 180
<212> TYPE: DNA
<213> ORGANISM: Xanthomonas oryzae pv.oryzae

<400> SEQUENCE: 3

```
atgggcaact ctctgaacac cc

-continued ctttaagaag gagatatacc atgggcaact ctctgaacac ccagttcggt g 51

<210> SEQ ID NO 7
<211> LENGTH: 60
<212> TYPE: DNA
<213> ORGANISM: Artificial Sequence
<220> FEATURE:
<223> OTHER INFORMATION: The sequence is synthesized.

<400> SEQUENCE: 7
tttccggttc gtccggcagt tcttcgatac gcgggttagc cgatccgcca ccgccagagc 60

<210> SEQ ID NO 8
<211> LENGTH: 60
<212> TYPE: DNA
<213> ORGANISM: Artificial Sequence
<220> FEATURE:
<223> OTHER INFORMATION: The sequence is synthesized.

<400> SEQUENCE: 8
gctctggcgg tggcggatcg gctaacccgc gtatcgaaga actgccggac gaaccggaaa 60

<210> SEQ ID NO 9
<211> LENGTH: 95
<212> TYPE: DNA
<213> ORGANISM: Artificial Sequence
<220> FEATURE:
<223> OTHER INFORMATION: The sequence is synthesized.

<400> SEQUENCE: 9
agaccagagg tgttcagaga cgatccgcca ccgccagagc cacctccgcc tgaaccgcct 60
ccaccgtctt cgattttagc ttcaccgaag attat 95

<210> SEQ ID NO 10
<211> LENGTH: 50
<212> TYPE: DNA
<213> ORGANISM: Artificial Sequence
<220> FEATURE:
<223> OTHER INFORMATION: The sequence is synthesized.

<400> SEQUENCE: 10
gctctggcgg tggcggatcg tctctgaaca cctctggtct gggtgcttct 50

<210> SEQ ID NO 11
<211> LENGTH: 49
<212> TYPE: DNA
<213> ORGANISM: Artificial Sequence
<220> FEATURE:
<223> OTHER INFORMATION: The sequence is synthesized.

<400> SEQUENCE: 11
gtggtggtgg tggtggtgct cgagtttacc accagaagaa gaaccctga 49

What is claimed is:

1. A multivalent plant immune fusion protein comprising SEQ ID NO: 1.

2. A method for promoting plant growth in a plant comprising (a) preparing a solution comprising the fusion protein of claim 1, wherein the solution may optionally further comprise one or more components selected from the group consisting of pesticides, fertilizers, soil conditioners, plant stimulants or plant extracts; and subsequently (b) performing a foliar spray or root irrigation upon the plant using the solution of (a), thereby resulting in the promotion of plant growth.

3. A nucleic acid encoding the multivalent plant immune fusion protein of claim 1 comprising SEQ ID NO: 2.

4. A recombinant vector, wherein the recombinant vector comprises the nucleic acid of claim 3.

5. A recombinant bacterium, wherein the recombinant bacterium comprises the nucleic acid of claim 3.

* * * * *